(12) United States Patent
McGuckin, Jr. et al.

(10) Patent No.: US 7,445,632 B2
(45) Date of Patent: Nov. 4, 2008

(54) PERCUTANEOUS AORTIC VALVE

(75) Inventors: James F. McGuckin, Jr., Radnor, PA (US); Peter W. J. Hinchliffe, Campbell Hall, NY (US)

(73) Assignee: Rex Medical, L.P, Conshohocken, PA (US)

( * ) Notice: Subject to any disclaimer, the term of this patent is extended or adjusted under 35 U.S.C. 154(b) by 193 days.

(21) Appl. No.: 11/222,570

(22) Filed: Sep. 9, 2005

(65) Prior Publication Data
US 2006/0009841 A1    Jan. 12, 2006

Related U.S. Application Data

(63) Continuation of application No. 10/429,536, filed on May 5, 2003, now Pat. No. 6,974,476.

(51) Int. Cl.
*A61F 2/24* (2006.01)
(52) U.S. Cl. ..................................... 623/2.37
(58) Field of Classification Search ............. 623/1.24, 623/2.1–2.42
See application file for complete search history.

(56) References Cited

U.S. PATENT DOCUMENTS

| | | | |
|---|---|---|---|
| 5,545,214 A | 8/1996 | Stevens | |
| 5,571,215 A | 11/1996 | Sterman et al. | |
| 5,713,951 A | 2/1998 | Garrison et al. | |
| 5,716,370 A | 2/1998 | Williamson, IV et al. | |
| 5,718,725 A | 2/1998 | Sterman et al. | |
| 5,728,151 A | 3/1998 | Garrison et al. | |
| 5,755,783 A | 5/1998 | Stobie et al. | |
| 5,814,097 A | 9/1998 | Sterman et al. | |
| 5,924,424 A | 7/1999 | Stevens et al. | |
| 5,957,949 A | 9/1999 | Leonhardt et al. | |
| 5,972,030 A | 10/1999 | Garrison et al. | |
| 5,976,174 A | 11/1999 | Ruiz | |
| 6,010,531 A | 1/2000 | Donlon et al. | |
| 6,102,945 A | 8/2000 | Campbell | |

(Continued)

FOREIGN PATENT DOCUMENTS

EP    0920842    6/1999

(Continued)

*Primary Examiner*—Suzette J Gherbi
(74) *Attorney, Agent, or Firm*—Neil D. Gershon

(57) ABSTRACT

The present invention provides a valve configured for insertion on the proximal and distal sides of a heart valve annulus to replace the heart valve of a patient. The valve comprises a first substantially annular portion adapted to be positioned on a proximal side of the annulus of a patient and a second substantially annular portion adapted to be positioned on a distal side of the annulus of a patient, wherein at least one of the first and second substantially annular portions is movable towards the other portion to a clamped position to clamp around the annulus. The second portion has a flow restricting portion extending therefrom and is movable between a first position to permit the flow of blood and a second position to restrict the flow of blood. In one embodiment, the valve has a suture joining the first and second portions to draw the first and second portions into closer proximity and a cinch member to secure the suture to maintain the first and second portions in the clamped position. In another embodiment, the first and second portions are connected by a first segment which biases the first and second portions toward the clamped position.

11 Claims, 17 Drawing Sheets

U.S. PATENT DOCUMENTS

| | | |
|---|---|---|
| 6,171,320 B1 | 1/2001 | Monassevitch |
| 6,287,339 B1 | 9/2001 | Vazques et al. |
| 6,319,281 B1 | 11/2001 | Patel |
| 6,338,740 B1 | 1/2002 | Carpentier |
| 6,425,916 B1 | 7/2002 | Garrison et al. |
| 6,458,156 B1 | 10/2002 | Wan et al. |
| 6,730,121 B2 * | 5/2004 | Ortiz et al. .................. 623/2.17 |
| 2001/0007956 A1 | 7/2001 | Letac et al. |
| 2002/0173841 A1 | 11/2002 | Ortiz et al. |
| 2003/0055496 A1 | 3/2003 | Cai et al. |
| 2003/0069593 A1 | 4/2003 | Tremulis et al. |
| 2004/0088047 A1 | 5/2004 | Spence et al. |
| 2004/0127982 A1 | 7/2004 | Machold et al. |
| 2004/0215333 A1 | 10/2004 | Duran et al. |

FOREIGN PATENT DOCUMENTS

| | | |
|---|---|---|
| FR | 1386811 | 1/1965 |
| JP | 63234965 | 9/1988 |
| WO | WO 8802247 | 9/1986 |
| WO | WO 9956665 | 4/1999 |

* cited by examiner

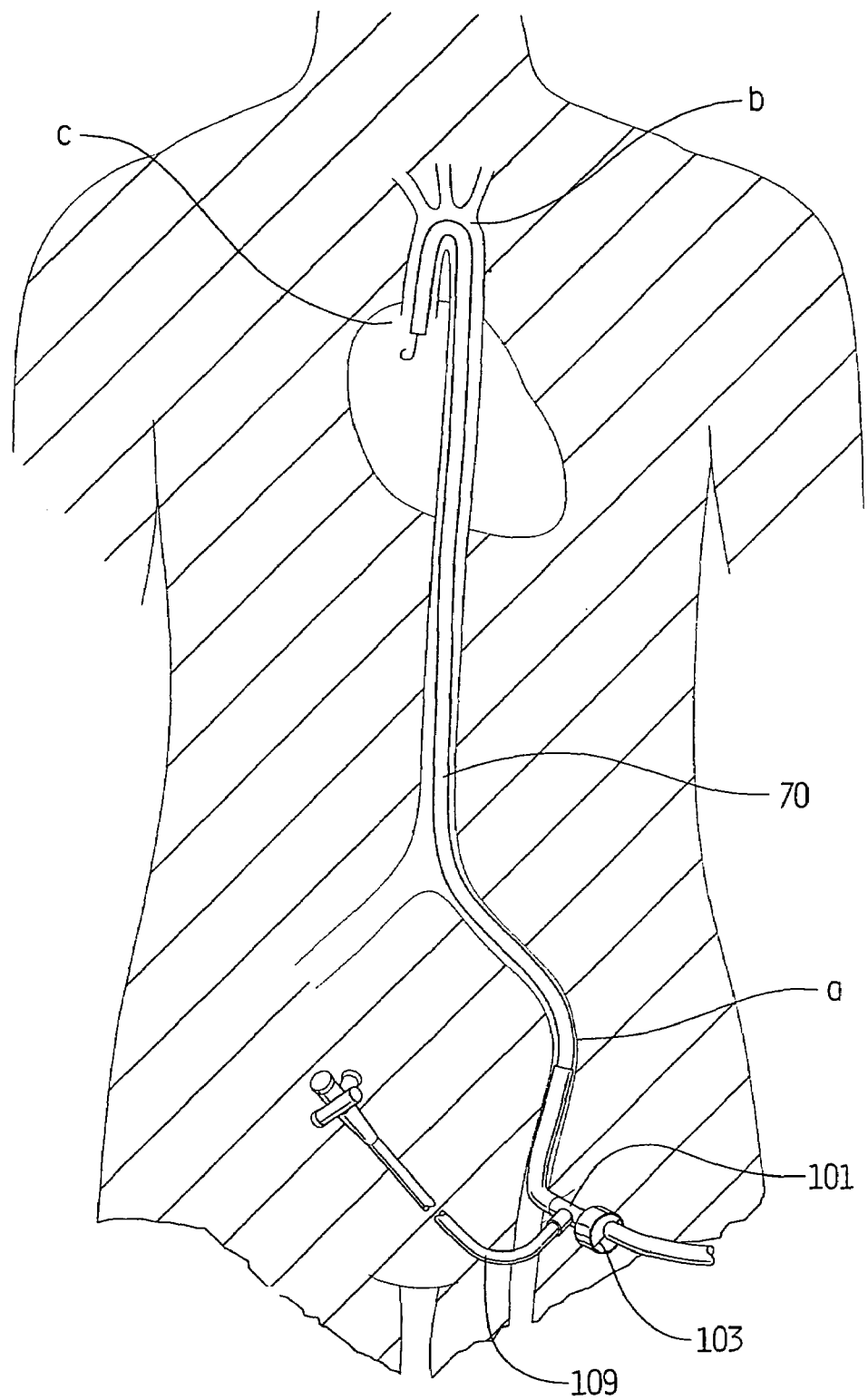
FIG_1A

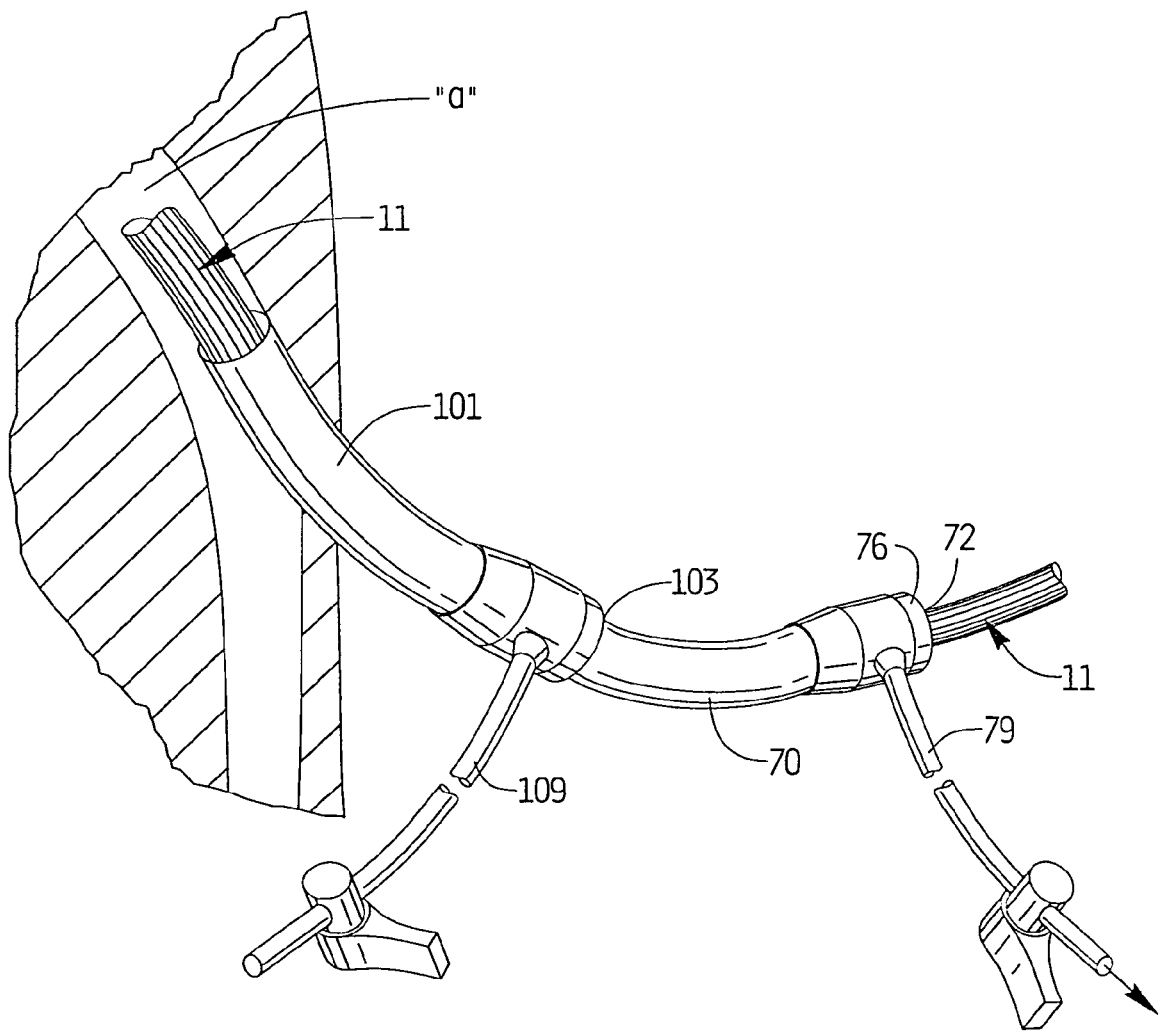
FIG_1B

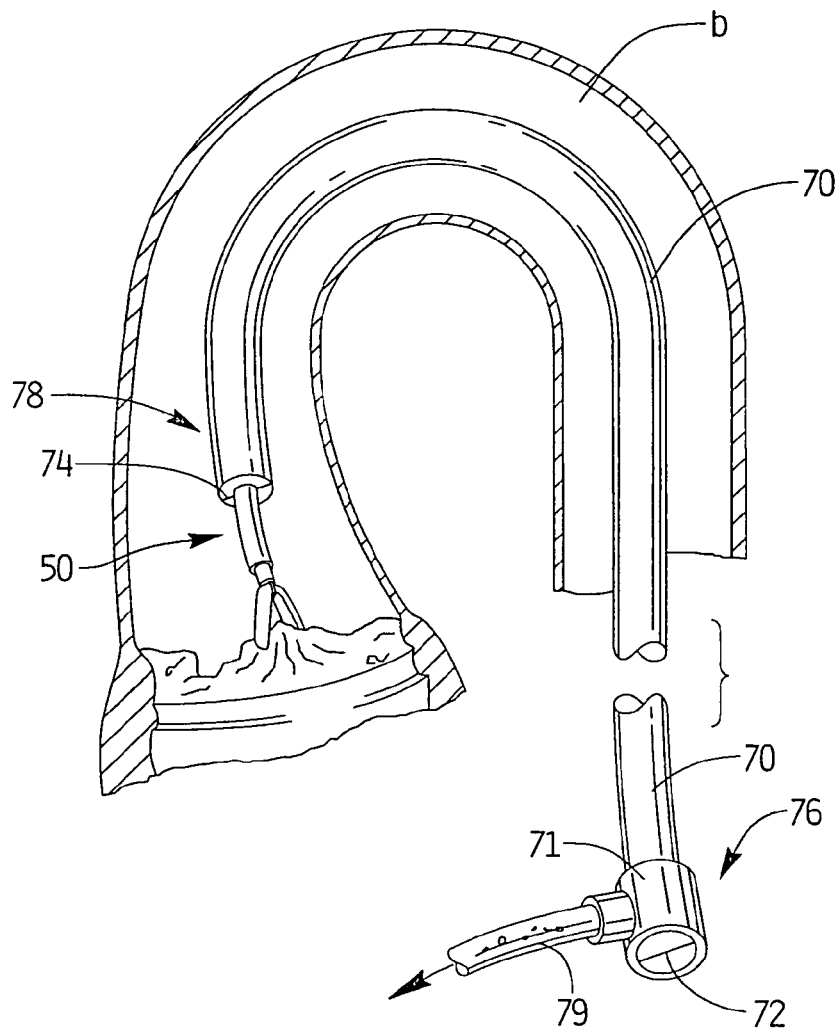
FIG_2A
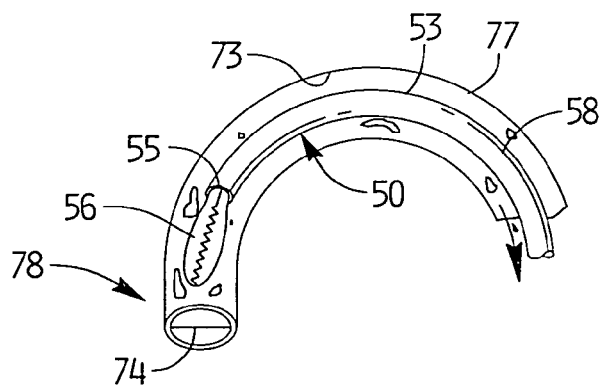
FIG_2B

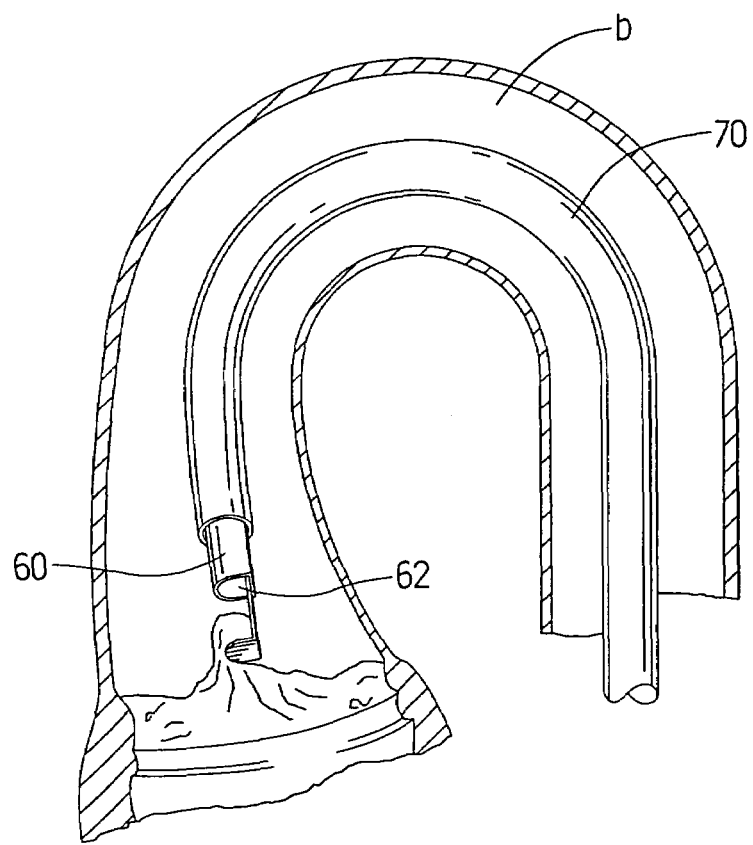
FIG_3
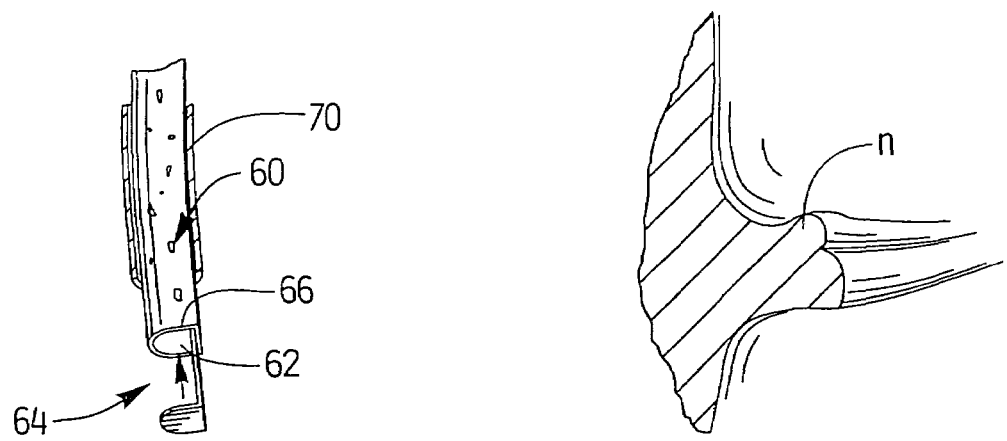
FIG_4
FIG_5

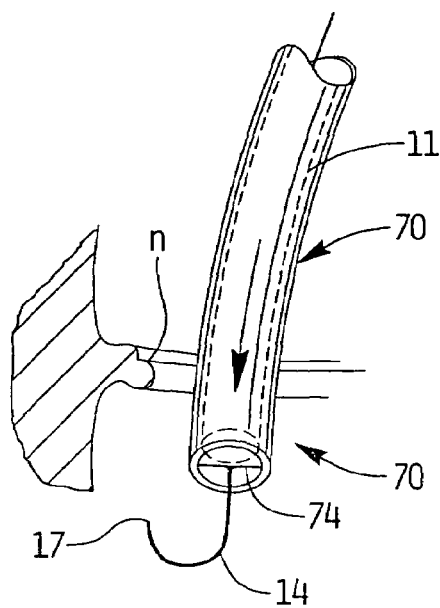
FIG_6
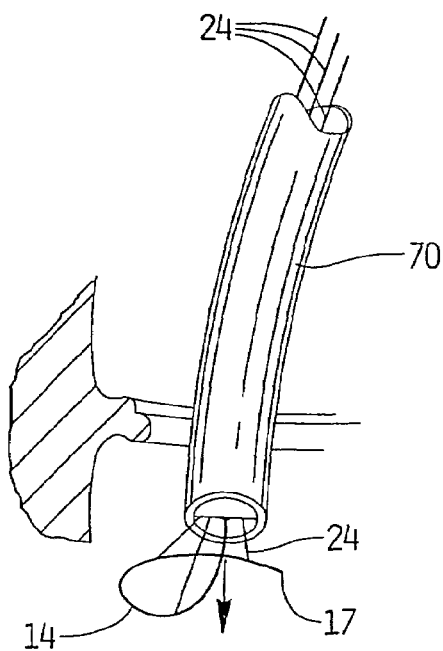
FIG_7A
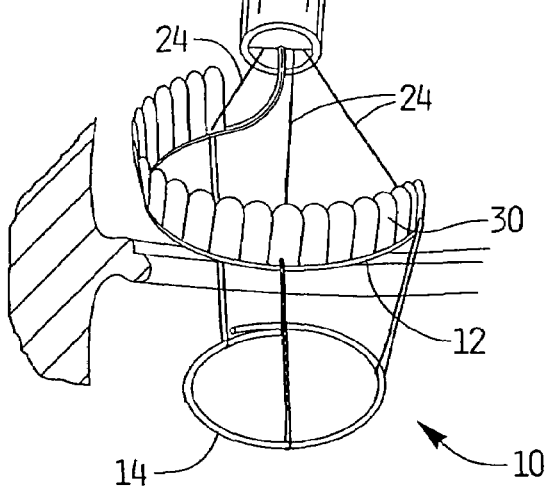
FIG_8

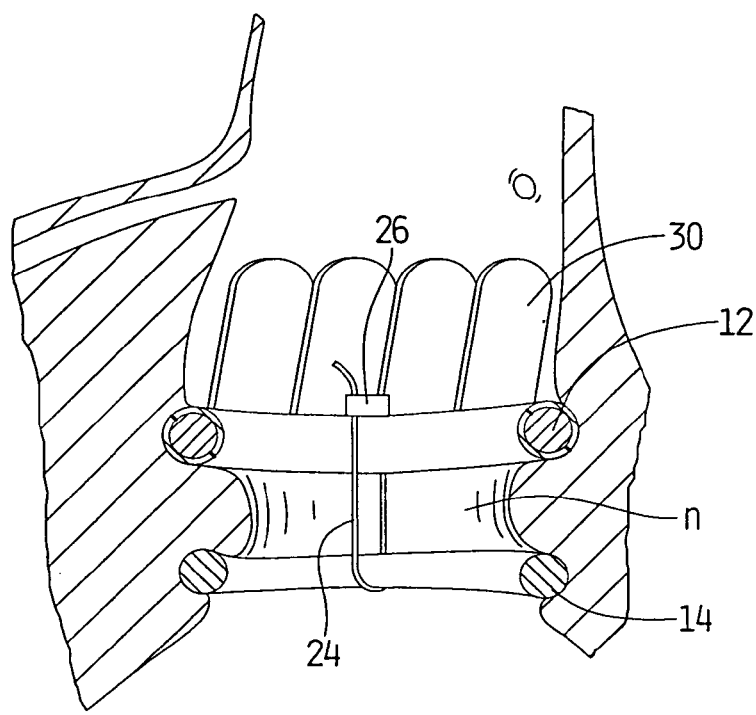
FIG_10A
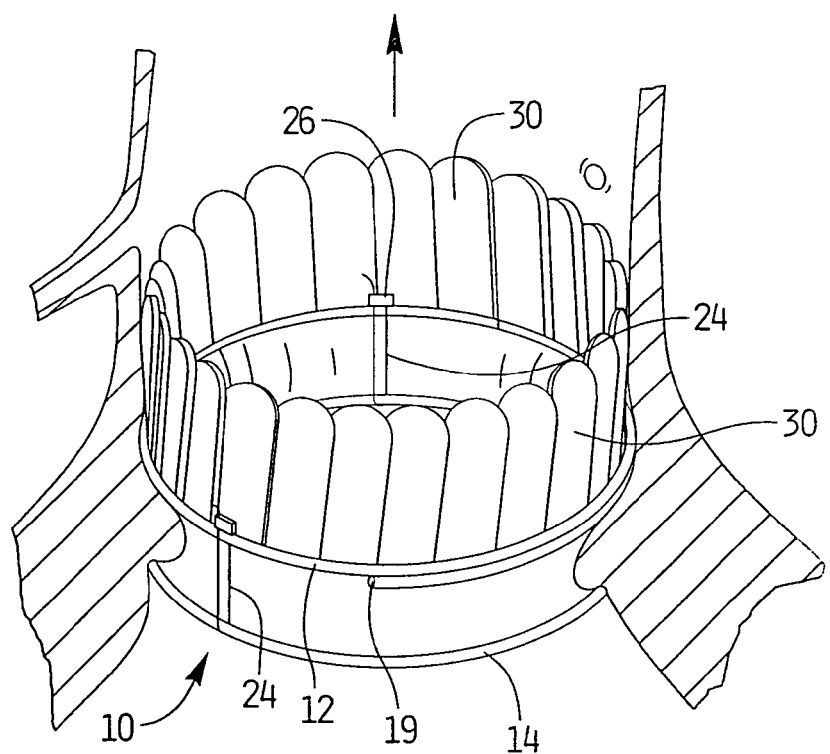
FIG_10B

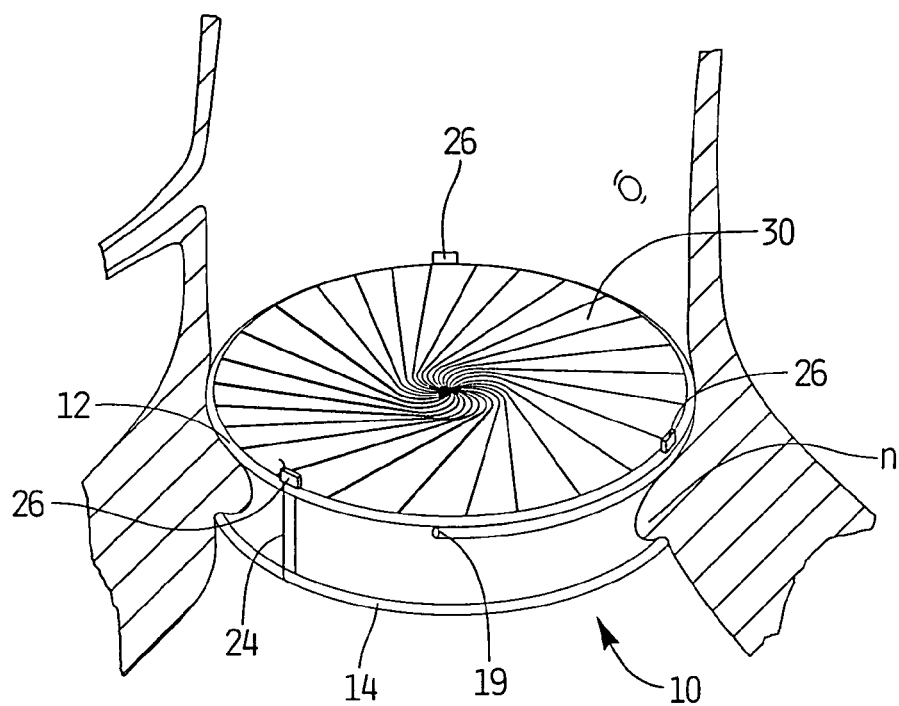
FIG_10C
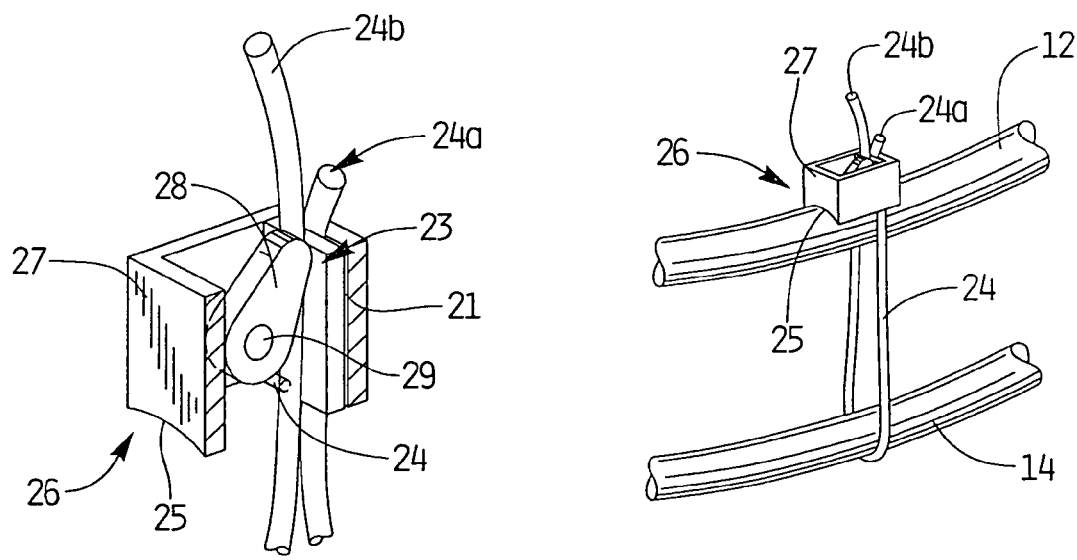
FIG_11A  FIG_11B

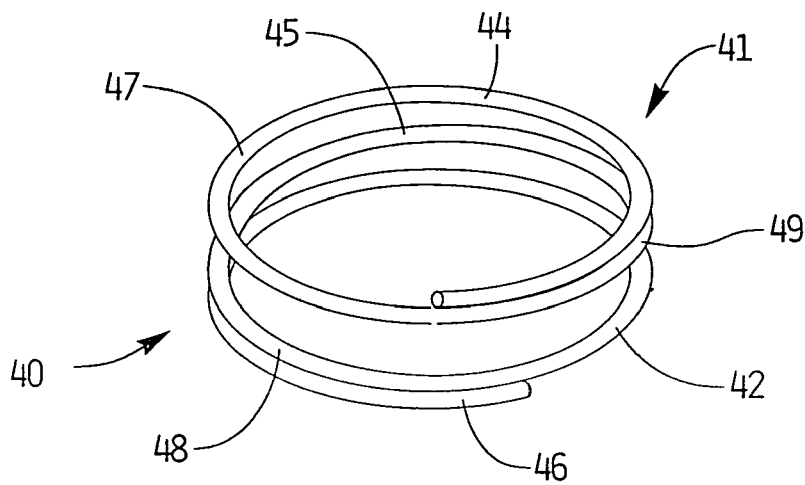
FIG_12A
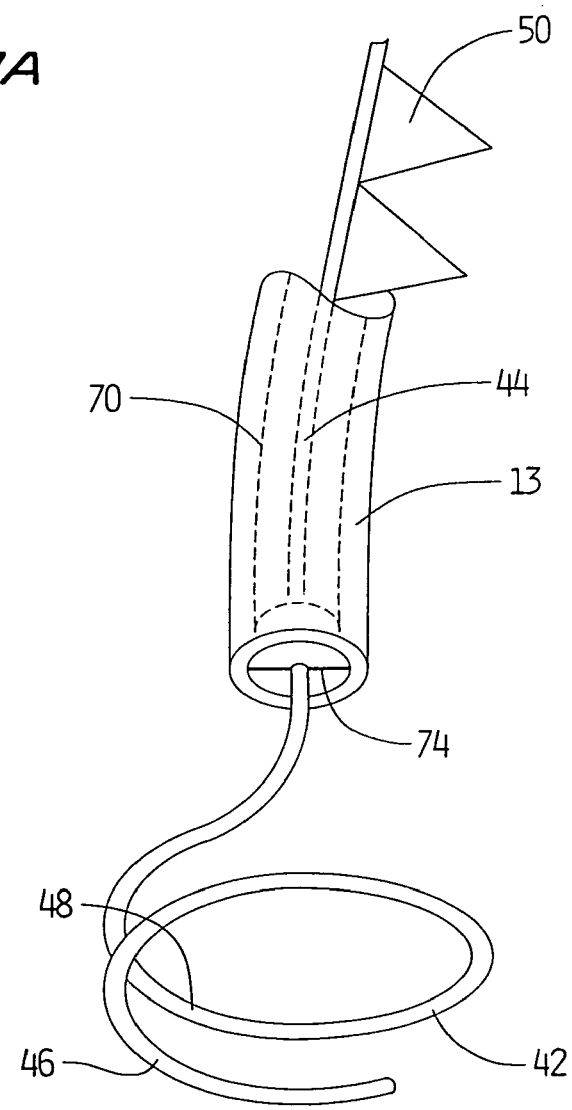
FIG_12B

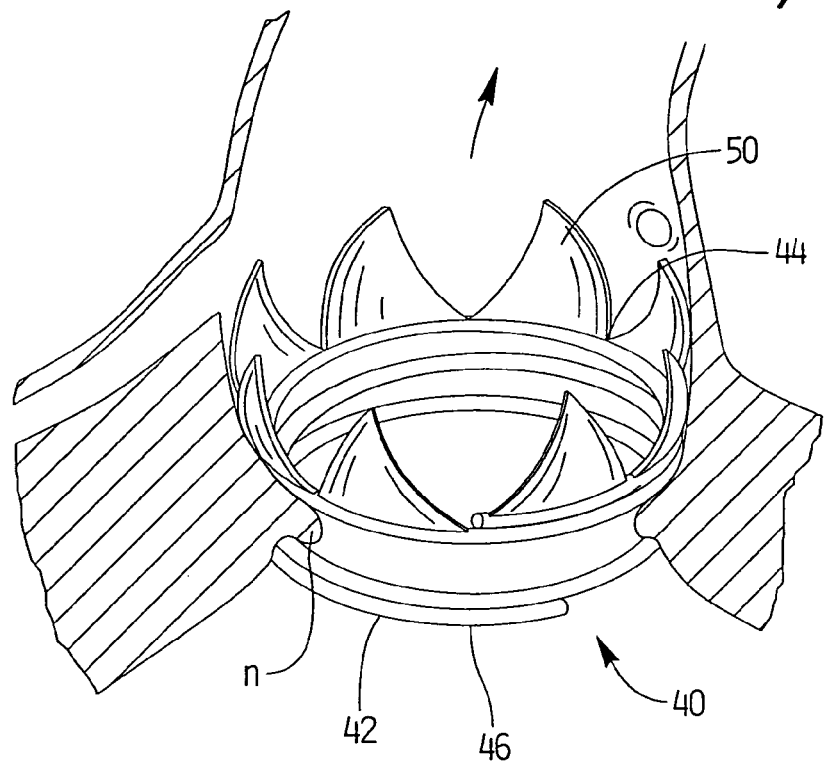
FIG_13
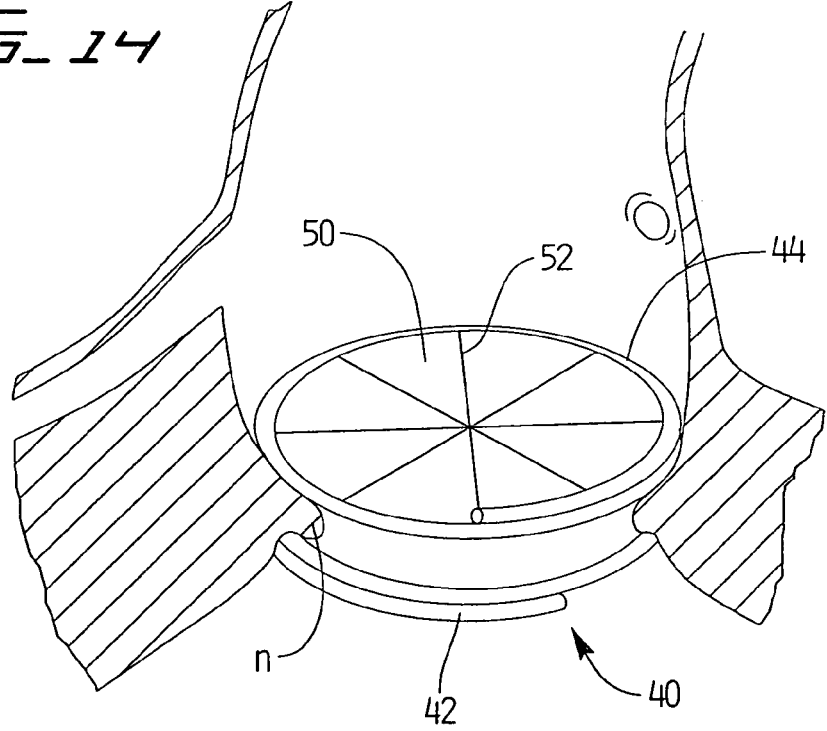
FIG_14

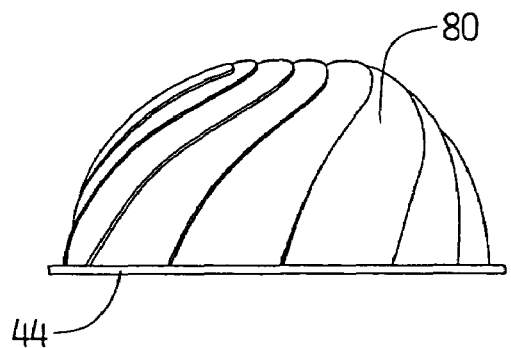
FIG_15
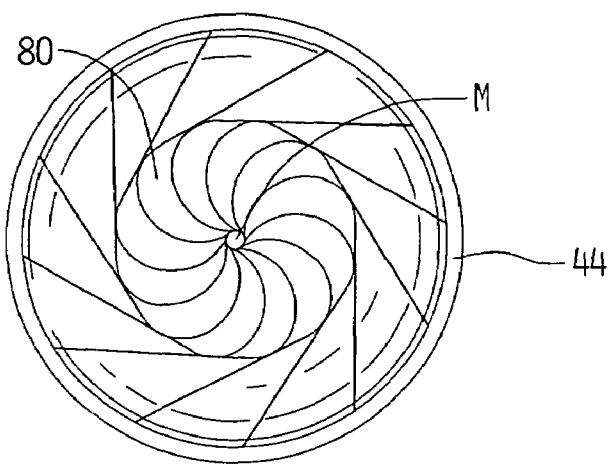
FIG_16
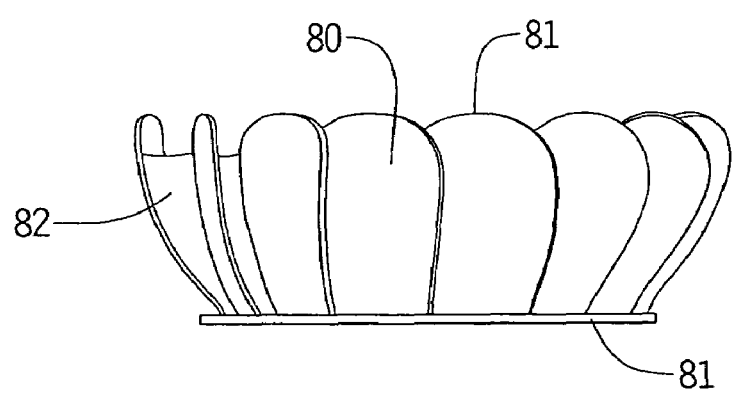
FIG_17

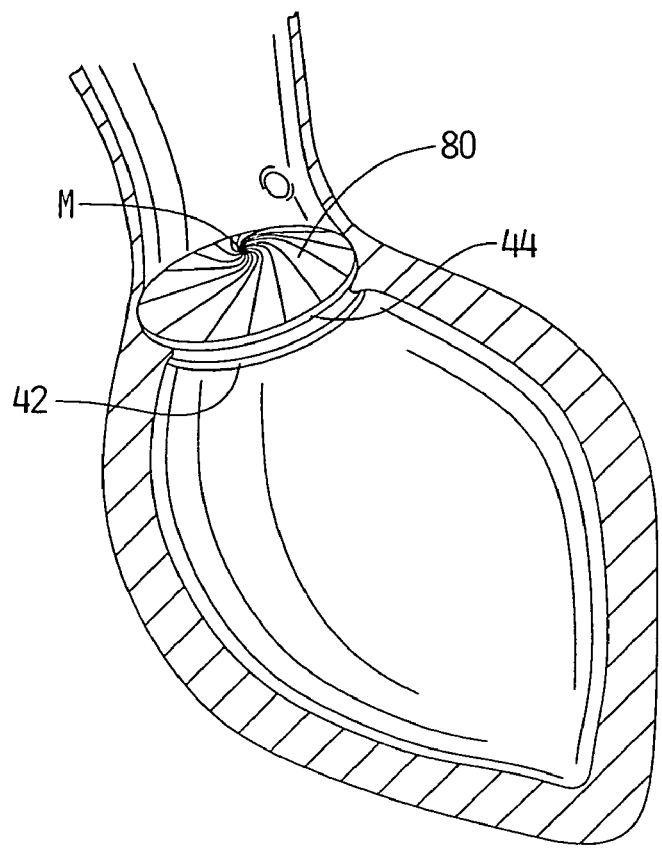
FIG_18
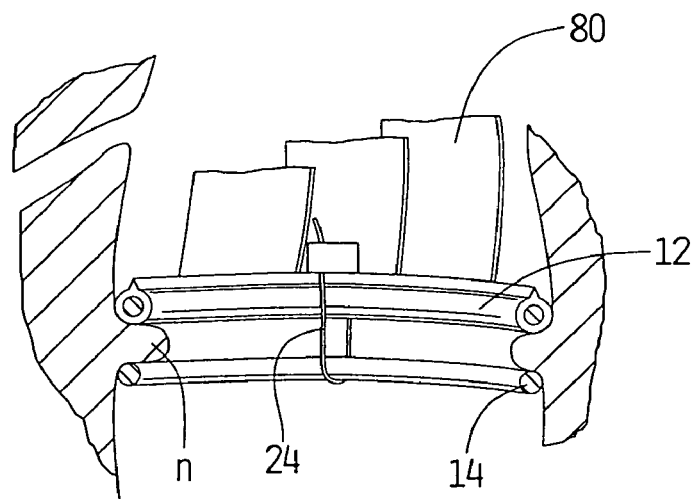
FIG_19

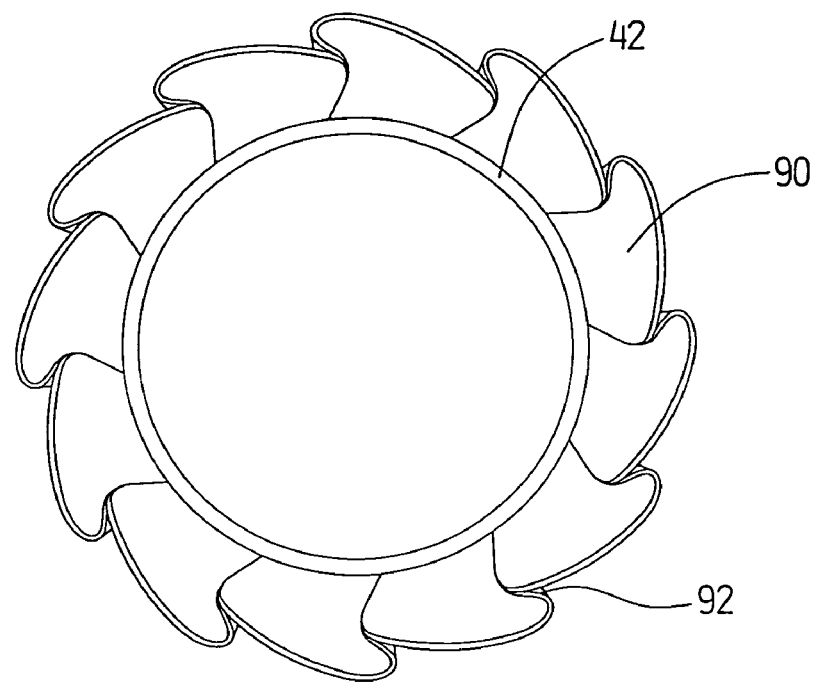
FIG_20
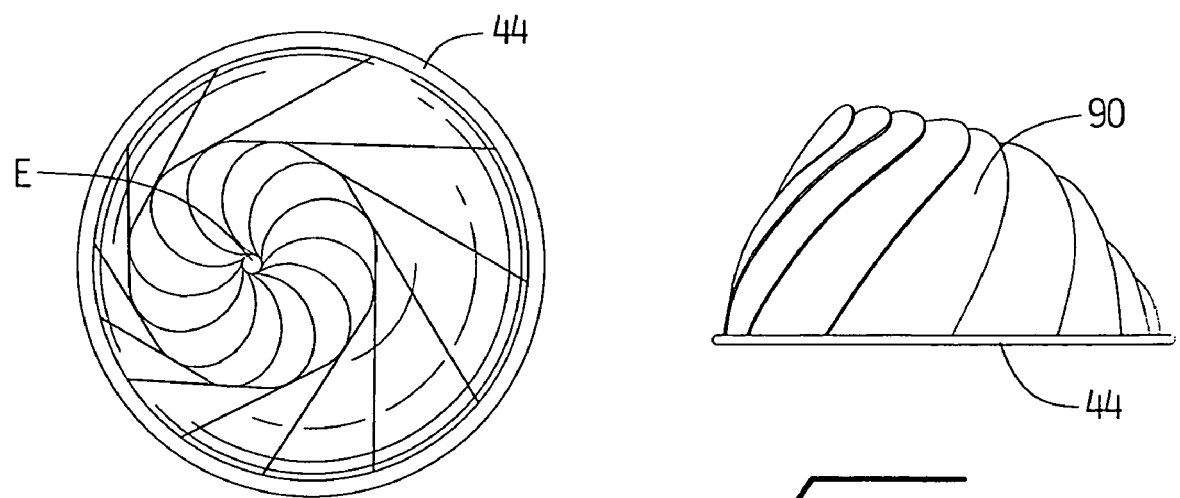
FIG_21
FIG_22

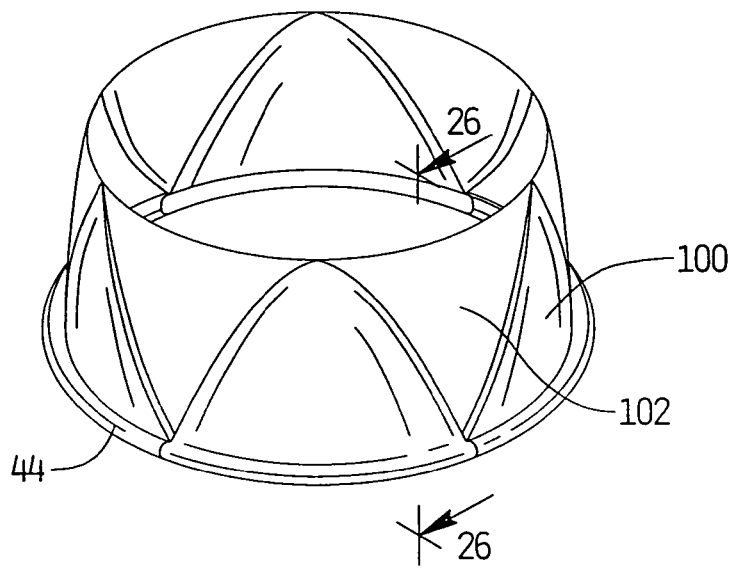
FIG_23
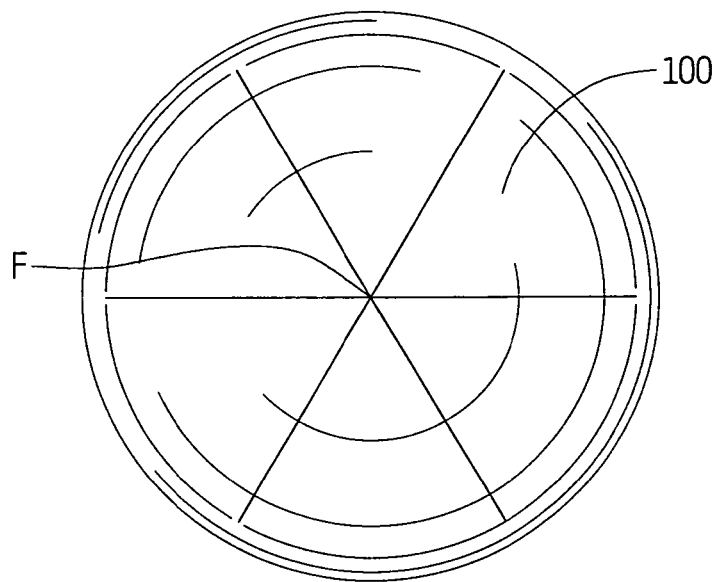
FIG_24
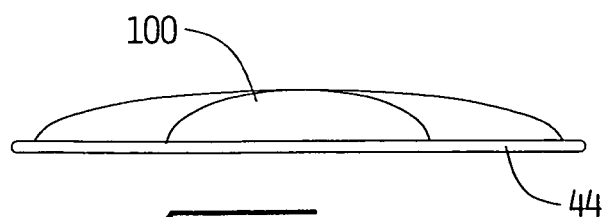
FIG_25
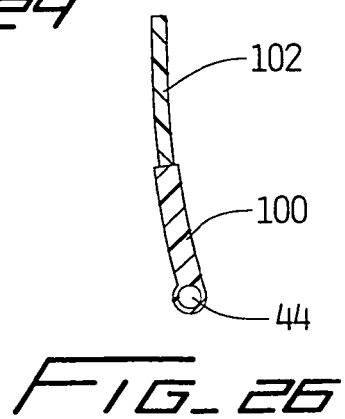
FIG_26

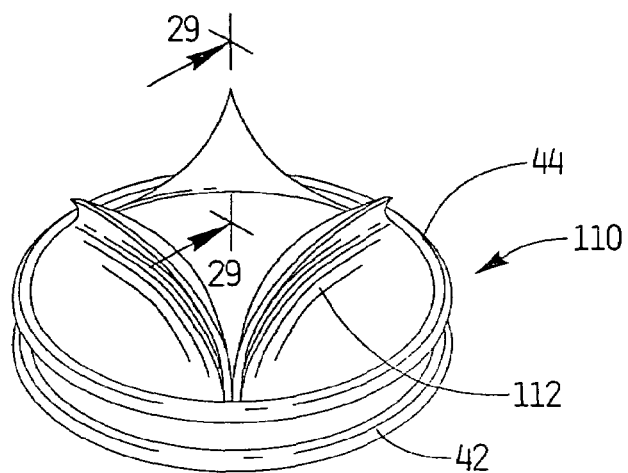
FIG_27
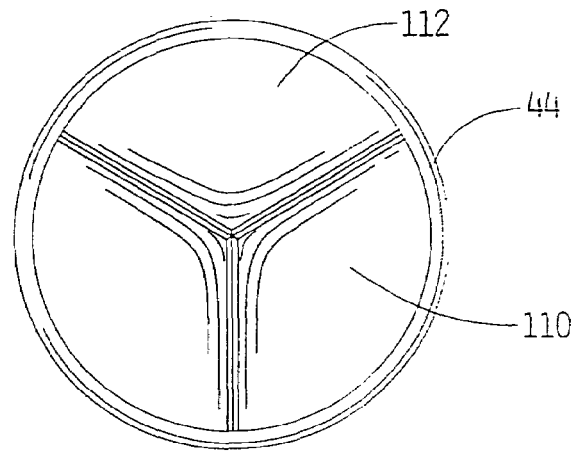
FIG_28
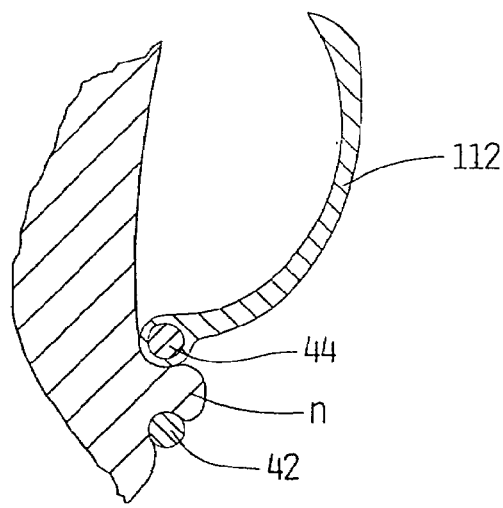
FIG_29
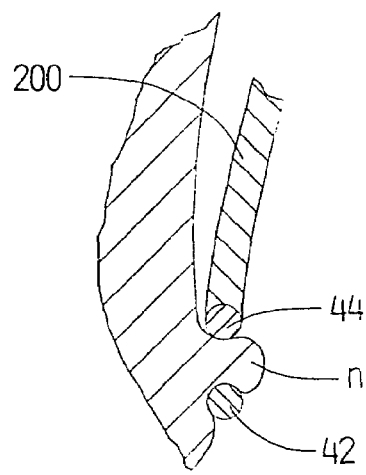
FIG_30

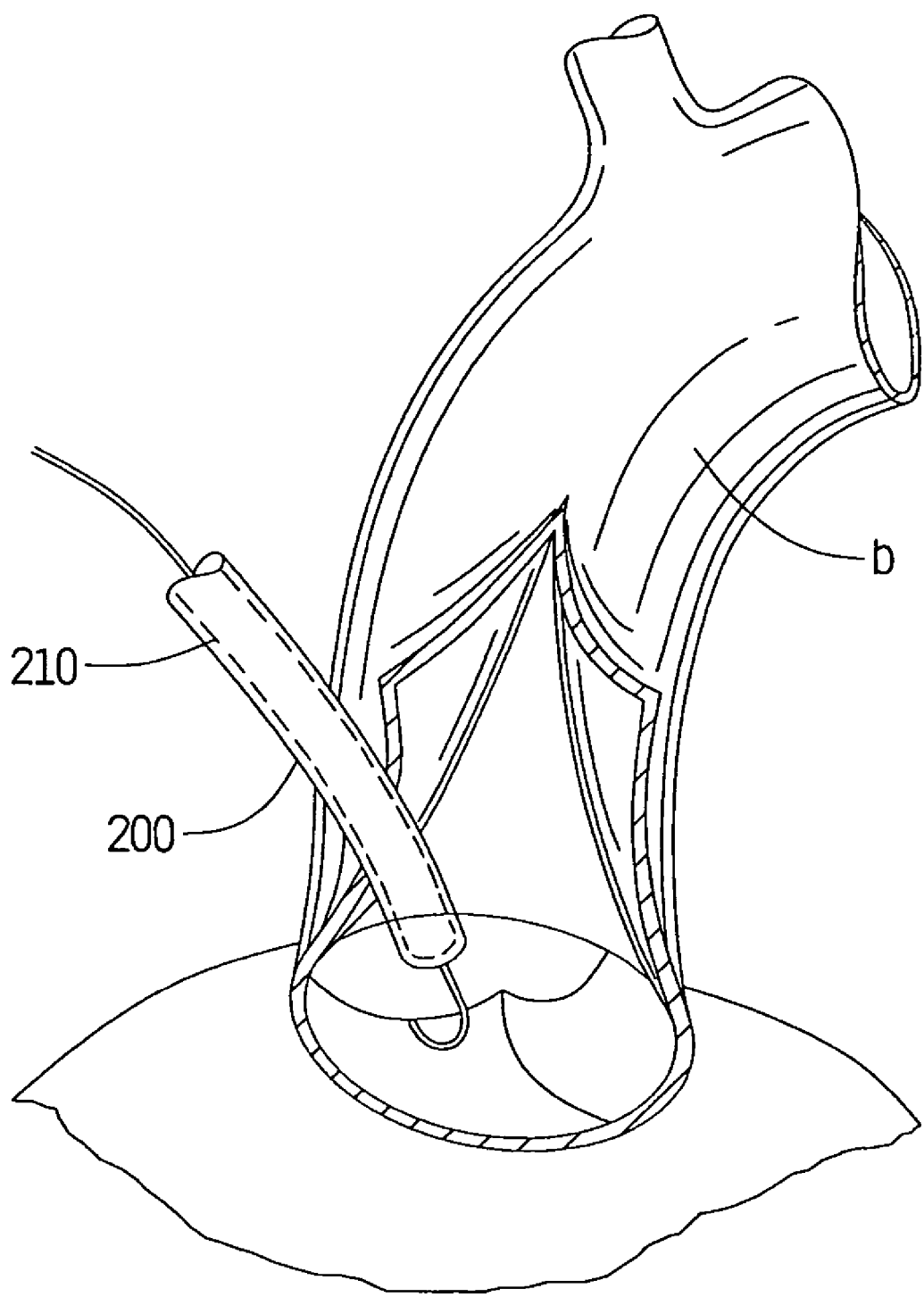
FIG_31

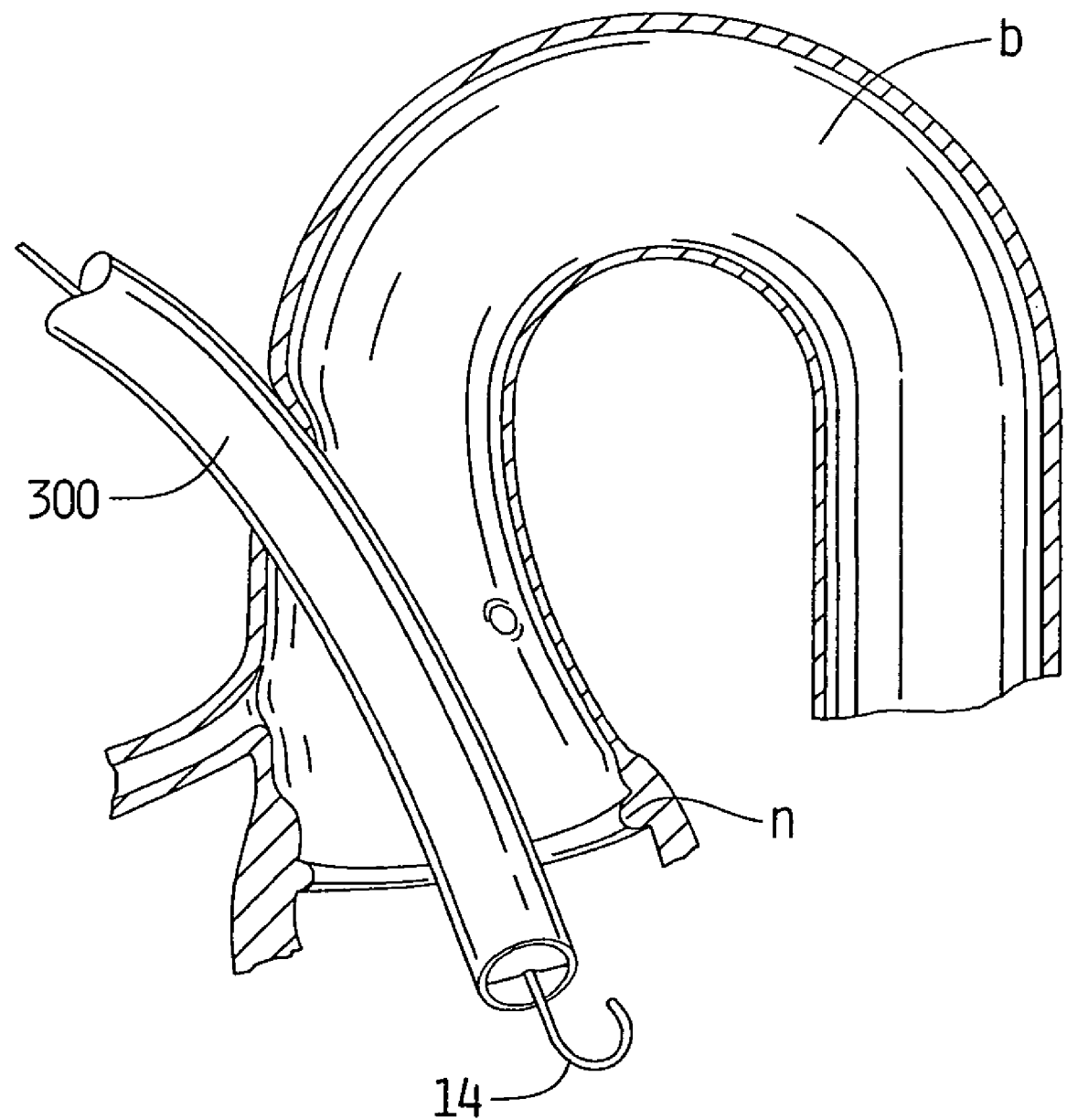

PERCUTANEOUS AORTIC VALVE

This application is a continuation of application Ser. No. 10/429,536, filed May 5, 2003 now U.S. Pat. No. 6,974,476.

This application claims priority from PCT application no. PCT/US/01/43879, filed Nov. 14, 2001 which claims priority from Provisional application No. 60/252,187, filed Nov. 21, 2000.

BACKGROUND

1. Technical Field

This application relates to a prosthetic valve and more particularly to a prosthetic valve for minimally invasive replacement of a patient's cardiac valve.

2. Background of Related Art

The aortic and mitral valves are heart valves that open and close automatically in response to the pumping of the heart to control blood flow. The aortic valve is open during ventricular systole, when the heart is in contraction and blood is surged through the aorta and pulmonary artery, and is closed during diastole, when the heart is in relaxation, dilates and the cavity fills with blood. The aortic valve is positioned between the left ventricle and ascending aorta and functions to prevent back flow into the ventricle. The mitral or bicuspid valve closes the orifice between the left atrium and the left ventricle to prevent back flow into the atrium.

If the aortic valve doesn't close properly after the heart pumps the blood through the valve into the aorta, blood will leak back into the heart. This oxygenated back flow of blood causes the heart to work harder and faster, thereby initially causing chest pain, fatigue, and reduced blood output from the heart, which over time can result in cardiomyopathy. Additionally, when the aortic valve is defective for a period of time, it oftentimes leads to mitral valve damage because the retrograde inflow of blood applies pressure against the mitral valve, preventing it from closing properly.

There are a variety of causes of heart valve malfunction, many resulting from infections or diseases such as congenital heart disease, calcification related to athrosclerosis, and fibrosis. Generally, there are two types of damaged valves: stenotic valve in which the valve does not open fully thereby limiting forward blood flow; and regurgitant valves in which the valve does not close properly thereby permitting back flow. In either instance, valve malfunction can leads to cardiomyopathy which is a disease of the heart muscle which if left untreated can lead to heart failure and death or post stenotic dilatation of the aorta which can lead to aneurysm.

If a defective heart valve cannot be surgically repaired, it may need to be removed and replaced with a replacement valve. Currently, the surgical technique for valve replacement is open heart surgery. This open surgery is quite traumatic because it requires a full sternotomy, namely cracking the patient's ribs and creating a chest incision extending almost along the entire length of the chest. This incision can be as long as 10-12 inches. Additionally, to perform the valve surgery, the patient's heart is stopped with cardioplegia and the patient is placed on a heart lung machine requiring withdrawing the blood from the venous side of the patient through blood flow tubes, transporting the blood to the heart lung machine for oxygenation, and delivering the oxygenated blood to the arterial side of the patient's body through blood inflow tubes. The problems and risks inherent with the heart lung machine are well documented. These include the risk of infection, trauma to the body as a result of the blood exchange, and the risk of brain damage or stroke. It is also been found that patients who undergo open heart surgery may suffer from permanent neurological lapses. Additionally, in stopping the heart and utilizing the heart lung machine, the aorta must be cross clamped to cut off the blood flow. This cross clamping can dislodge plaque inside the vessel, potentially sending it through the bloodstream to the brain and causing stroke. Moreover, open heart surgery, being a highly invasive procedure, requires a long patient recovery time. The long patient recovery time, the use of the heart lung machine, and the requirement for additional hospital staff, e.g. machine technicians, all add to the costs of the surgical procedure.

Recognition of the disadvantages and risks of open heart surgery has recently led to attempts at minimally invasive approaches. For example, smaller chest incisions, such as partial sternotomies or creating a "window" between adjacent ribs, are now being utilized in some instances to access the aorta for performing certain heart bypass procedures. However, these approaches still require cracking and/or retracting ribs and are surgically difficult not only due to the limited access and maneuverability of the instrumentation, but due to limited visibility. Additionally, the heart may need to be manipulated to provide proper access, potentially causing additional trauma. For these reasons, such minimally invasive approaches have found only limited applications in bypass procedures and to the inventors' knowledge have not been successfully used for aortic valve replacement surgery.

U.S. Pat. No. 5,571,215 discloses another approach to avoiding the aforementioned problems and risks associated with a full sternotomy, i.e. open heart surgery. In the '215 patent, a percutaneous endoscopic method for valve installation is disclosed. Basically a series of cannulas or trocars are inserted percutaneously, along with an endoscopic viewing device, and the valve replacement is performed through these small tubes with visualization on a remote video screen. To the inventors' knowledge, this form of endoscopic surgery is not currently being utilized, most likely because 1) access is limited; 2) the ability to manipulate the tissue and valve through small tubes is difficult; 3) visibility is limited; 4) and the small instrumentation needed for the procedure is limited. The problem with this endoscopic approach is compounded by the fact that the valve is sutured to the valve annulus. As can be appreciated, manipulating a suturing instrument through small tubes, with limited maneuverability and restricted visibility is quite difficult. Additionally, as with suturing in open procedures, the success of the suturing and knot tying can oftentimes be dependent on the particular skills of the surgeon. This method also requires opening the aorta, and ensuring proper closure after the surgery.

Therefore, to date, no surgical method is effective in avoiding the aforementioned disadvantages of open heart valve surgery. Thus, it would be advantageous to provide a minimally invasive method to insert and implant a heart valve, therefore avoiding the problems and risks associated with open surgery. It would also be advantageous to provide a replacement valve that can more easily be secured to the valve annulus without requiring the difficult, skill dependent and time consuming suturing and knot tying of the replacement valve.

SUMMARY

The present invention overcomes the disadvantages and deficiencies of the prior valves and valve insertion methods. The present invention provides a valve configured for insertion on the proximal and distal sides of a heart valve annulus to replace the heart valve of a patient. The valve comprises a first substantially annular portion adapted to be positioned on a proximal side of the annulus and a second substantially annular portion adapted to be positioned on a distal side of the annulus, wherein at least one of the first and second substantially annular portions is movable towards the other portion to a clamped position to clamp around the annulus. The second substantially annular portion has a flow restricting portion extending therefrom and is movable between a first position to permit the flow of blood and a second position to restrict the flow of blood.

The first and second portions are preferably comprised of shape memory alloy. In one embodiment, the valve has a suture joining the first and second substantially annular portions to draw them into closer proximity and a cinch member securing the suture to maintain the first and second portions in the clamped position. In another embodiment, the first and second portions are formed from a unitary wire and are connected by a wire segment which biases the first and second portions toward the clamped position. In this embodiment, the first substantially annular portion preferably underlies a first arcuate portion and a second arcuate portion preferably underlies the second substantially annular portion to form a coiled wire of multiple overlapping segments.

Various embodiments of flow restricting portions are provided. In one embodiment, the flow restricting portion comprises a plurality of leaflets extending circumferentially around the second portion in a direction away from the first portion and are foldable inwardly towards a convergence region at the midpoint of the second portion so the convergence region is concentric with the second portion to restrict blood flow. In another embodiment, the leaflets are foldable inwardly towards a convergence region offset from a midpoint of the second portion so the convergence region is eccentric with the second portion to restrict blood flow. The flow restricting portion may further include a membrane joining adjacent leaflets to cooperate with the leaflets to restrict blood flow when the leaflets are in the closed position.

A replacement cardiac valve implantation system is also provided comprising a valve and a delivery member. The valve comprises a wire element having a first ring-like portion and a second ring-like portion positioned over the first ring like portion. At least the first ring like portion is movable towards and away from the second ring-like portion and is biased towards the second ring like portion. The delivery member introduces the wire element into a patient's body, such that the first ring-like portion is placed on a first side of the annulus and the second ring-like portion is placed on a second side of the annulus, the bias of the portions forcing the first ring-like portion in closer proximity to the second ring-like portion to secure the valve in a clamped position around the annulus. The first and second ring-like portions are preferably joined by an arcuate wire segment extending therebetween which biases the first and second ring-like portions to a clamped position.

A method of installing a valve to replace a heart valve of a patient is also provided comprising:

positioning a valve in a first configuration inside a first catheter;

inserting the first catheter through the femoral artery;

advancing the first catheter around the aortic arch so that a distal end portion of the first catheter is adjacent an annulus of a patient;

ejecting a first portion of the valve from the first catheter to position it on a first side of the annulus; and ejecting a second portion of the valve from the first catheter on a second side of the annulus allowing the first and second portions of the valve to clamp around both sides of the annulus.

BRIEF DESCRIPTION OF THE DRAWINGS

Preferred embodiment(s) of the present invention are described herein with reference to the drawings wherein:

FIG. 1A is an isometric view showing the delivery catheter being inserted percutaneously though the left femoral artery to access the aortic valve annulus;

FIG. 1B is an enlarged perspective view of the proximal portion of the delivery catheter shown inserted into a conventional sheath;

FIG. 2A is a broken view of a percutaneously inserted valve resector shown extending through the delivery catheter and around the aortic arch to minimally invasively resect the aortic valve, and further showing the resected tissue being suctioned from the delivery catheter;

FIG. 2B illustrates the resector of FIG. 2A withdrawn into the delivery catheter, proximal of the slit valve, with the resected tissue being suctioned through the catheter;

FIG. 3 is a broken view of a percutaneously inserted rongeur shown extending around the aortic arch and protruding through the delivery catheter to minimally invasively resect the aortic valve;

FIG. 4 is a perspective view of the rongeur of FIG. 3 with a portion of the delivery catheter removed to show the resected tissue being suctioned through the rongeur;

FIG. 5 is a perspective view of the valve annulus of the patient;

FIG. 6-9 illustrate the steps of insertion of the valve of a first embodiment of the present invention wherein FIG. 6 is a perspective view showing the partial ejection of the first wire element from the delivery catheter to a position on the proximal side of the annulus;

FIG. 7A is a perspective view showing the first wire element further ejected from the catheter for deployment on the proximal side of the annulus to form a first or proximal ring;

FIG. 8 is perspective view showing full deployment of the first and second wire elements to form the first and second rings positioned on the proximal and distal sides of the annulus, respectively, and showing a first embodiment of the valve leaflets in the open position (with several of the leaflets removed for clarity);

FIG. 9 is a perspective view of the delivery catheter and a sectional view of the first and second rings fully deployed and the suture being tightened to clamp the rings on the annulus;

FIG. 10A is a partial cross-sectional view illustrating the valve of FIGS. 6-9 in the clamped position around the annulus with the cinch mechanism in the locking position;

FIG. 10B is a perspective view of the valve of FIGS. 6-9 in the clamped position with the leaflets in the open position to allow blood flow in the direction of the arrow;

FIG. 10C is a perspective view of the valve of FIGS. 6-9 in its clamped position with the leaflets in the closed position to stanch blood flow;

FIG. 11A is a perspective view of the cinch mechanism of FIG. 10A for retaining the suture with part of the housing removed for clarity;

FIG. 11B is a perspective view showing the cinch mechanism of FIG. 11A attached to a top surface of the distal ring;

FIG. 12A is a perspective view of a second embodiment of the valve of the present invention;

FIG. 12B is a perspective view showing initial deployment of the valve of FIG. 12A from a delivery catheter to form a first (proximal) ring;

FIG. 13 is a perspective view showing the valve of FIG. 12 clamped on the annulus with a second embodiment of the leaflets in the open position to allow blood flow;

FIG. 14 is a perspective view showing the valve of FIG. 13 clamped on the annulus with the leaflets in the closed position to stanch blood flow;

FIG. 15 is a side view of a third embodiment of the valve leaflets in a closed position shown having a curved overlapping configuration;

FIG. 16 is a top view of the valve of FIG. 15 showing the overlapping leaflets in a closed configuration, concentric with the ring, to restrict blood flow;

FIG. 17 is a side perspective view of the valve leaflets of FIG. 15 in the open position showing the membrane joining adjacent leaflets;

FIG. 18 is a perspective view showing the valve of FIG. 12, with the leaflet configuration of FIGS. 15-17, in the closed position and clamped on the annulus;

FIG. 19 is a side view of the valve of FIGS. 6-9, with the leaflet configuration of FIGS. 15-17, shown clamped on the annulus and in the open configuration, with only a few of the leaflets shown for clarity;

FIG. 20 is a bottom view of a fourth embodiment of the valve leaflets of the present invention;

FIG. 21 is a top view of the valve leaflets of FIG. 20 shown in a closed position eccentric with the second (distal) ring;

FIG. 22 is a side view of the valve of FIG. 20 showing the eccentric leaflets in the closed position;

FIG. 23 is a perspective view of a fifth embodiment of the valve leaflets of the present invention, having a membrane joining adjacent leaflets, shown in the closed position;

FIG. 24 is a side view of the valve of FIG. 23 shown in the closed position;

FIG. 25 is a top view of the valve of FIG. 23 shown in the closed position;

FIG. 26 is a cross sectional view taken along lines 26-26 of FIG. 23 showing the varying thickness of the valve leaflets and membrane;

FIG. 27 is a perspective view of a sixth embodiment of the valve leaflets of the present invention shown in the open position to allow blood flow;

FIG. 28 is a top view of the valve of FIG. 27 showing the leaflets in the closed position to restrict blood flow;

FIG. 29 is a cross-sectional view taken along lines 29-29 of FIG. 27 showing the leaflets threaded onto the second (distal) ring;

FIG. 30 is a cross-sectional view of an alternate way to attach the leaflets showing the leaflets attached to the upper surface of the second ring;

FIG. 31 is a perspective view of an alternate approach to inserting the valve of the present invention; and FIG. 32 is a perspective view of another alternate approach to inserting the valve of the present invention.

DETAILED DESCRIPTION OF PREFERRED EMBODIMENTS

Figure 7B:
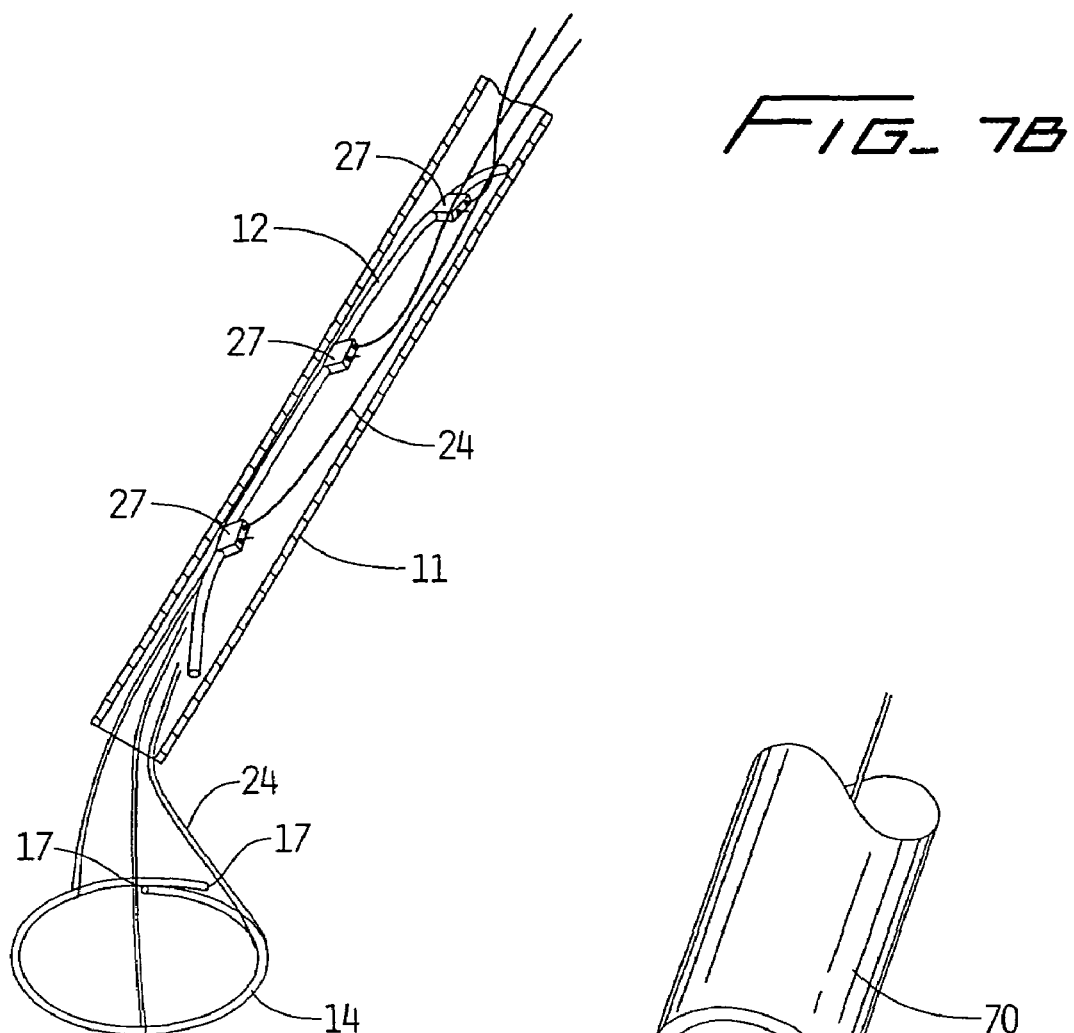
FIG. 7B is a perspective view showing the first ring fully ejected from the valve retaining catheter (the delivery catheter removed for clarity) and with the catheter sectioned to illustrate the positioning of the second wire element and suture cinch mechanisms therewithin.

Referring now in detail to the drawings where like reference numerals identify similar or like components throughout the several views, FIGS. 6-10 illustrate a first embodiment of the heart valve of the present invention and FIGS. 12-14 illustrate a second embodiment of the heart valve of the present invention, each valve configured and dimensioned for minimally invasive insertion and implantation in a patient's body. Various leaflet embodiments for use with either valve are disclosed in FIGS. 15-30 and described in detail below.

The valve of the present invention, designed to replace the patient's aortic valve, is contained within a valve retaining catheter and inserted through a delivery catheter 70 as shown in FIGS. 1A and 1B. Delivery catheter 70 is retained within a conventional sheath 101 having a side arm or tube 109 for flushing the surgical site. Sheath 101 has a slit valve 103 to seal around the delivery catheter 70 when inserted therethrough. Delivery catheter is inserted through the femoral artery "a" in the patient's leg, directed through the aortic arch "b" and into the left ventricle "c" of the patient. The valve is then deployed around the annulus, (a naturally formed tissue collar) in the manner described below to thereby form a replacement prosthetic valve to provide the function of the aortic valve. It should be understood that although the various embodiments of valves of the present invention are described below for replacement of the aortic valve, the valves of the present invention could also be used to replace other valves such as the mitral valve.

The valve of the present invention, as can be appreciated, is inserted intraluminally (or percutaneously through the femoral artery) so the aorta does not need to be penetrated to provide access to the annulus. To complement the intraluminal implantation of the valve, instrumentation is provided to resect the natural valve of the patient intraluminally. Thus, by providing a percutaneous valve resector, an entire percutaneous system is provided since the resection of the natural valve as well as insertion and implantation of the replacement valve can be achieved percutaneously, e.g. through a small incision into the femoral artery in the patient's leg. The intraluminal insertion avoids a sternotomy or partial sternotomy and its associated risks and disadvantages discussed above. FIGS. 2-5 illustrate two examples of instrumentation to percutaneously (intraluminally) remove the defective aortic valve.

Turning first to FIGS. 2A and 2B, a first embodiment of a valve resecting instrument is designated by reference numeral 50. Resecting instrument 50 is inserted through delivery catheter 70. Delivery catheter 70 is inserted through a small incision in the patient's leg to access the femoral artery (not shown), retained within sheath 101 (see FIG. 1), and advanced through the femoral artery and around the aortic arch "b" to access the patient's defective valve. Delivery catheter 70 has slit valves 72, 74 on its proximal and distal ends 76,78, respectively, to maintain a fluid seal when surgical instruments are inserted into the lumen 77 of the delivery catheter 70. Thus, blood and debris are prevented from entering into the lumen 77 except for removal of resected valve tissue as described below. Delivery catheter 70 has a side tube or arm 79 connected to a suction source to remove the resected valve tissue.

Resecting instrument 50 has a flexible outer tube 58, a pair of resecting jaws 56 extending from a distal end 55 of the outer tube 58, and a jaw manipulator such as a wire (not shown) mechanically connected to the jaws 56 to manipulate the jaws 56 between open and closed positions to resect the valve. Resecting jaws 56 of resecting instrument 50 are controlled from a proximal end of outer tube 58, which extends proximally of slit valve 72 to provide access to the surgeon outside the patient's body. Thus, the wire or controller is manipulated from outside the body to resect the valve. The resected valve tissue is suctioned through the slit valve 74 (the negative pressure opening the valve 74) and through delivery catheter lumen 77, in the space between inner wall 73 of delivery catheter 70 and outer wall 53 of resecting instrument 50, as shown in FIG. 2B. Alternatively, a separate suctioning instrument can be placed alongside the resecting instrument 50 within the delivery catheter 70. The pressure of the blood from the aorta can aid in pushing the debris out through the valve 74.

An alternate embodiment of the valve resector is shown in FIGS. 3 and 4. A flexible rongeur 60 is depicted having a central lumen 62 to suction the resected pieces of the valve therethrough. FIG. 4 illustrates a distal end portion 64 of the rongeur 60, with a portion of delivery catheter 70 removed, to show the tissue being removed through the lumen 62. The rongeur 60 is inserted through the delivery catheter 70 in the same manner as the aforedescribed resecting instrument 50. To resect tissue, the tissue is placed between end plate 64 and cutter 66. Plate 64 is retracted in the direction of the arrow, or alternately the cutter 66 is advanced toward the plate 64, thereby forcing the tissue against cutter 66 for resecting the valve. The resected tissue is suctioned through lumen 62.

FIG. 5 illustrates the patient's anatomy with the aortic valve removed to enable implantation of a replacement valve. The annulus is designated by letter "n" and due to its annular collar like configuration, provides a natural mount or clamping surface for the valve of the present invention which will become apparent from the discussion below.

Turning now to the first embodiment of the valve illustrated in FIGS. 6-9, and referring first to FIG. 8, the valve 10 includes a first wire forming a first or proximal ring 14 and a second separate wire forming a second or distal ring 12. The first and second wire rings 14, 12 are joined by a series of sutures 24. Although three sutures 24 are shown, additional or fewer sutures can be utilized. The wire can alternatively be composed of a unitary element so that the proximal and distal rings form a unitary piece joined by a wire portion therebetween. The wire can be made of stainless steel, but is preferably composed of shape memory material such as Nitinol (nickel-titanium alloy). Shape memory alloy enables the wires to be retained inside the valve retaining catheter 11 in an elongated position, extending along the longitudinal axis of the catheter 11 as shown in FIG. 7B, and return to a preconfigured, memorized configuration when deployed from the catheter. Consequently, the proximal and distal rings can be positioned in the catheter, one behind the other or even adjacent each other in a substantially straight position, thereby allowing a small diameter delivery catheter to be utilized. This is best illustrated in FIG. 7B which illustrates the distal ring 14 deployed from the valve retaining catheter 11 but the proximal ring 12 still retained in its straightened configuration inside the catheter 11. Note that both the distal and proximal wire rings 14 12 have atraumatic tips, such as a ball tip 17, 19, respectively, at their exposed ends.

A pusher (not shown) ejects the first or proximal wire ring 14 by contact with a proximal end, enabling it to return to its substantially annular configuration. After ejection of the first ring 14, either the same pusher, or a separate pusher proximal to or alongside the first pusher, ejects the distal wire ring 12 by advancing it from its proximal end, allowing it also to return to its substantially annular configuration. The sutures 24 which wrap around and hold the rings together, are ejected as the rings 12, 14 are ejected.

Figure 9:
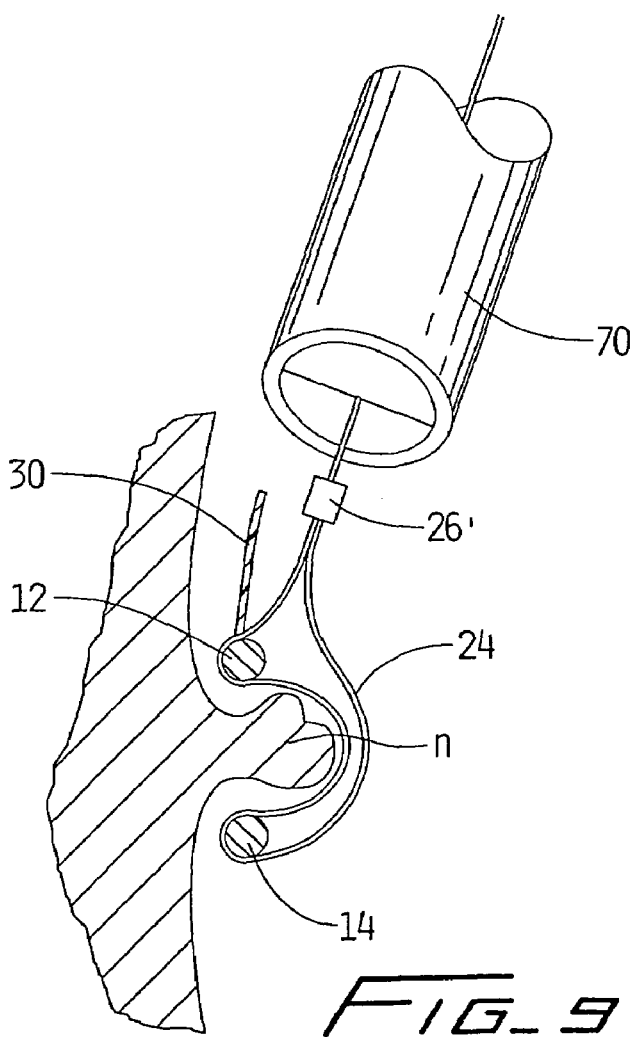

Three sutures 24 are provided, preferably about 120 degrees apart as shown. Each suture is wrapped around the rings 12 and 14 as best shown in FIGS. 7B, 9 and 11B, and are tensioned to draw the rings 12 and 14 toward each other. A cinch mechanism 26 comprising a housing 27 and pivotable locking element 28 (see FIG. 11A) is provided for each suture. Housing 27 has a convex surface 25 to conform to an outer surface of the distal ring 12 to enable it to rest atop ring 12 and is preferably welded or adhesively attached thereto. Alternatively, housing 27 can be provided with a longitudinally extending opening to receive the distal wire therethrough.

One end 24a of each suture 24 is secured within slot 21 and the other end 24b is retained between locking element 28 and inner wall surface 23. End 24b, prior to being cut, extends beyond the length of the catheter, exiting through the proximal end. The suture is tensioned by pulling from its proximal end, thereby moving the two rings 12, 14 towards each other into locking engagement. Locking element 28, spring biased as shown, prevents movement of the suture in a distal direction to maintain the suture and respective rings in a clamped (locked) position.

A series of leaflets or petals 30 extend upwardly from the distal ring 12 along the entire circumference as seen in FIGS. 8 and 10B. (Only some of the leaflets are shown in FIG. 8 for clarity.) Leaflets 30 are preferably attached to distal ring 12 by welding or adhesives; however, other methods of attachment as known in the art can also be utilized. Leaflets 30 are movable from an open position as shown in FIG. 10B to allow blood flow from the heart to the aorta to a closed position shown in FIG. 10C, where their end portions are curved and converge to a closed position to prevent blood flow. The point of convergence as shown is aligned with a center region of the rings 12, 14.

The steps of deploying and securing the valve 10 will now be described. First, the delivery catheter 70 is inserted through a conventional sheath, over a conventional guidewire (not shown) through the femoral artery, around the aortic arch, and down to the aortic valve area adjacent the valve annulus (the aortic valve having already been removed). As shown in FIG. 6 the distal end 76 of the delivery catheter 70 is placed slightly past of the valve annulus, i.e. on the "inner" side of the annulus, also referred to herein as the proximal side of the annulus, relative to the heart. The guidewire is then removed. Valve retaining catheter or valve sheath 11, with the aortic valve 10 contained therein in an elongated orientation, with the leaflets folded, is inserted through the delivery catheter 70 and likewise advanced through the femoral artery, around the aortic arch to adjacent the valve annulus.

The first wire element, which will form the first or proximal (inner) ring 14, is initially advanced from the valve retaining catheter 11 and through the slit valve 74 of the delivery catheter 70 to the position of FIG. 6, ensuring it is on the proximal side of the annulus "n", relative to the heart. FIG. 7A illustrates further advancement of the first wire element to enable it to return to its memorized configuration to form proximal annular ring 14 (see also FIG. 7B). After deployment of the ring 14, the second wire element is ejected from valve retaining catheter 111 through slit valve 74 of delivery catheter 70, allowing it to return from its straightened configuration within the valve retaining catheter 11 to its memorized configuration, shaped to form an annular second ring 12 on the distal (outer) side of the annulus, as shown in FIG. 8. The sutures are wrapped around the rings 12 and 14 as shown, with housing 27 of cinch mechanism 26 attached to the second ring 12 so the sutures are ejected with the rings 12, 14.

Once the wire elements are fully deployed and the positioning of the first and second rings 14, 12 on respective sides of the annulus is confirmed by visualization techniques such as ultrasound, the rings 14, 12 are pulled together by tensioning the suture 24. The surgeon manually pulls on the proximal end of each suture which extends proximally of the delivery catheter 70 and valve retaining catheter 11 outside the body. The two rings 12, 14 are thus pulled tightly together to clamp around the annulus with the cinch mechanism 26 ensuring that the suture is secured to lock the rings in this clamped position. The excess suture is cut at proximal end 24b and the valve retaining catheter 11 and delivery catheter 70 are withdrawn, leaving the valve 10 secured around the annulus. As noted above, although described for aortic valve replacement, the valve 10 described herein can be used to replace other valves such as the mitral valve. It should also be noted in FIG. 9, the cinch mechanism 26' is shown spaced from the distal ring 12, it being contemplated that the cinch mechanism can alternatively be slid into engagement with the distal ring 12 by a pusher (not shown), and attached thereto by conventional means such as a snap fit.

An alternate (second) embodiment of the valve of the present invention is illustrated in FIGS. 12-14 and designated generally by reference numeral 40. Valve 40 includes a coiled wire element preferable of unitary construction which forms a first or proximal (inner) ring 42 and a second or distal (outer) ring 44. The rings 42 and 44 are joined by an arcuate wire segment 45 which also functions to bias the rings 42 and 44 toward each other as discussed below.

As shown, the first ring 42 has a 360 degree segment 46 which extends into overlying partially annular or arcuate segment 48, preferably ranging from about 90 to about 180 degrees. Second ring 44 likewise has a 360 degree segment 47 extending into underlying partially annular or arcuate segment 49, preferably ranging from about 90 to about 180 degrees. Thus, in the illustrated embodiment each ring 42, 44 can be considered to circumscribe at least about a 450 degree segment forming a coiled wire of multiple overlapping segments. Arcuate segment 48 transitions into arcuate segment 49 in the transition area defined by wire segment 45 extending at an angle to the parallel planes defined by each of the rings 42, 44.

A series of substantially triangular leaflets 50 extend from the second ring 44, preferably attached thereto by adhesive, although other means of attachment are also contemplated. When in the closed position of FIG. 14, leaflets 50 converge at a concentric point 52, aligned with the midpoint of rings 42, 44 to close off blood flow. As in the valve of the first embodiment, the rings 42, 44 are placed on opposing sides of the annulus, i.e. on proximal and distal sides of the annulus relative to the heart. The bias of wire segment 45 forces the rings 42, 44 together to clamp against the annulus.

The wire element is preferably composed of a shape memory material, such as Nitinol, having the memorized configuration of FIG. 12A. Thus, the wire element is contained in the valve retaining catheter or valve sheath 13 in a longitudinally straightened position, with the leaflets folded, to reduce the profile for insertion. In use, delivery catheter 70 is inserted into a conventional sheath (e.g. sheath 101 of FIG. 1A) and advanced over a guidewire through the femoral artery as described above with the distal end of the delivery catheter 70 placed on the "inner" or proximal side of the annulus. Next, valve retaining catheter 13 with the wire element contained therein is inserted through the slit valve 72 of the delivery catheter 70 and advanced around the aortic arch to terminate adjacent the distal end of delivery catheter 70. A pusher element pushes the wire element distally outside the valve retaining catheter 13 and delivery catheter 70. FIG. 12B illustrates wire element initially advanced. (Note that FIG. 12B shows the leaflets 50 in the unfolded condition for clarity, it being understood that the leaflets would be folded or compressed within the valve retaining catheter 13 to reduce the profile).

When the wire element is deployed, the first ring segment reverts from it straightened configuration inside the valve retaining catheter 13 to the memory configuration of FIG. 12B, thus forming a first (proximal) ring 42 with an overlying segment 48. Once the position of the proximal ring 42 is confirmed using applicable visualization techniques, the wire element is further deployed, allowing the second wire to return to its memory configuration to form a second or distal ring 44 with underlying segment 49. The rings 42, 44 are then forced together by wire segment 45 to the position of FIG. 14, with the rings 42,44 clamped on opposing sides of the annulus. Thus, sutureless attachment to the annulus is achieved.

FIG. 14 illustrates the valve leaflets 50 in the closed position, where they converge at their tips during diastole. Their systolic or open position is illustrated in FIG. 13. It should be appreciated that the rounded edge, curved leaflets of the embodiment of FIG. 8 could alternatively be used with the valve of the second embodiment of FIG. 12-14.

Various alternate embodiments of valve leaflets are disclosed in FIG. 15-30 and will now be described. The leaflets need to accommodate two competing requirements: long term stability to handle repeated opening and closing without inverting or undesirably contacting the vessel wall and flexibility for unimpeded opening and closing to simulate natural valve function. The embodiments described below are intended to strike a balance between these two requirements. It should be understood that these leaflet configurations could be used with either of the two valve embodiments 10, 40 described above. Additionally the leaflets can be attached to the surface of the distal ring by welding, adhesive, insert molding or other means. Alternatively, the distal ring can extend directly through the leaflets to secure the leaflets to the ring.

Turning first to FIGS. 15-18, in this embodiment, leaflets 80, having rounded edges 81, are connected by a membrane 82 of sheet material. The membrane 82 will add to the stability of the leaflets by reducing the likelihood of inversion or "floppy valve" and may minimize post stenotic valve fibrillation or beating/trauma against the aortic wall. The leaflets 80, when closed, converge in a partially overlapping fashion to a midpoint "M" concentric with the distal and proximal rings, i.e. aligned with the centerline of the rings. The curved or spiral-like overlapping configuration will also add to the stability of the leaflets and reduce the likelihood of leakage. FIG. 18 illustrates the leaflets 80 utilized with the embodiment of FIGS. 12-14 and FIG. 19 illustrates the leaflets 80 utilized with the embodiment of FIGS. 6-10.

In the embodiment of FIG. 20-22, the leaflets 90 are curved and also have a membrane 92 joining adjacent leaflets. However, the leaflets 90, when closed into their curved partially overlapping configuration converge to a point "E" eccentric with respect to the distal and proximal rings. Thus, the convergence point "E" of the leaflets 90 is offset with respect to the centerline of the rings. This offset will direct blood flow toward the side of the vessel rather than in the center of the vessel as in the concentric leaflets of FIGS. 15-17.

FIGS. 23-25 illustrate another embodiment of leaflets of the present invention. Leaflets 100 are connected by a membrane 102 to increase the stability of the leaflets. The membrane 102 joins adjacent leaflets, however, alternatively, the membrane can extend around the entire periphery of the leaflets, functioning to further prevent leakage when the valve is closed. As shown in the cross sectional view of FIG. 26, the leaflets 100 have a thickness greater than the thickness of the membrane 102. This will increase stability towards the base of the leaflets, i.e. closer to the distal ring 44, while increasing flexibility towards the top or outer portion of the leaflets. In the closed position, the leaflets 11 converge at point "F", aligned with the center point of the rings.

The foregoing membranes can be composed of polyethylene, PTFE, or other suitable materials. Additionally, flexible metallic struts, made from materials such as Nitinol, can also be embedded in the membrane 82 to provide additional support.

A porcine or tricuspid valve is illustrated in FIGS. 27-30. This valve configuration more closely resembles the natural valve of the patient. In this embodiment, the tricuspid valve 110 having three leaflets 112 can be connected to the top of distal ring 44 as shown in FIG. 29.

FIG. 30 illustrates an alternative way to attach the leaflet. In this version, the ring 44 extends directly through the leaflets 200, e.g. the leaflets are threaded onto the wire ring.

ALTERNATE APPROACHES

As discussed above, the valves of the present invention are designed for percutaneous (intraluminal) insertion through the femoral artery. However, the inventors have realized that some surgeons might prefer either a full or partial sternotomy before transitioning to a minimally invasive approach. Some surgeons may also prefer the "window" approach which involves an incision between, and retraction of, the ribs of a patient. The valves of the present invention provide an advantage even if performing a sternotomy or "window" approach since they avoid the time consuming and complicated steps of suturing the valve to the annulus. FIG. 31 illustrates how either valve of the present invention can be inserted through the aorta, in an open or more invasive surgical procedure. A portion of the aortic wall would be dissected as shown, and a delivery catheter 200 containing a valve retaining catheter 210 would be inserted therethrough. The valve 10 or 40 would be deployed from the valve retaining catheter 210 in the manner described above, and clamp against the annulus to provide sutureless attachment to the annulus as described above.

Although the endoscopic approach has not been clinically accepted for reasons suggested above, in the event this approach becomes accepted, the valve 10 and 40 of the present invention would provide an advantage because of their sutureless attachment to the annulus. FIG. 32 illustrates such insertion of the valve through an endoscope 300 in a thoracoscopic approach to valve replacement.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A valve configured for insertion on the proximal and distal sides of a heart valve annulus to replace the heart valve of a patient, the valve comprising:

a first substantially annular portion adapted to be positioned on a first side of the annulus of a patient, the first portion movable from an elongated reduced profile position for insertion to a substantially annular position for placement;

a second substantially annular portion adapted to be positioned on a second side of the annulus of a patient, at least one of the first and second substantially annular portions being movable towards the other portion to a clamped position to clamp around the annulus, the second substantially annular portion having a flow restricting portion extending therefrom and movable between a first position to permit the flow of blood and a second position to restrict the flow of blood, the second portion and flow restricting portion movable from an elongated reduced profile position for insertion to a substantially annular position for placement;

the first and second portions being comprised of unitary wire, the unitary wire including an arcuate wire segment extending between the first and second portions, the wire biasing the first and second portions toward each other in the substantially annular position, and the first and second annular portions each circumscribe a segment greater than 360 degrees to form an overlapping segment, and the arcuate wire segment extends along an arc greater than 90 degrees.

2. The valve of claim 1, wherein the flow restricting portion comprises a plurality of leaflets extending from the second portion in a direction away from the first portion, the leaflets extending circumferentially around the second portion and foldable inwardly towards a convergence region at the midpoint of the second portion so the convergence region is concentric with the second portion to restrict blood flow.

3. The valve of claim 1, wherein the flow restricting portion comprises a plurality of leaflets extending from the second portion in a direction away from the first portion, the leaflets extending circumferentially around the second portion and foldable inwardly towards a convergence region offset from a midpoint of the second portion so the convergence region is eccentric with the second portion to restrict blood flow.

4. The valve of claim 1, wherein the wire is composed of a shape memory alloy.

5. The valve of claim 4, wherein the wire has a shape memorized position when the wire is in the substantially annular position for placement.

6. The valve of claim 1, wherein at least a portion of the first and second portions lie in parallel planes, and the wire segment extends at an angle to the parallel planes.

7. The valve of claim 6, wherein the wire is composed of a shape memory alloy.

8. The valve of claim 7, wherein the wire has a shape memorized position when the wire is in the substantially annular position for placement.

9. The valve of claim 1, wherein the first substantially annular portion underlies a first arcuate portion and the second substantially annular portion overlies a second arcuate portion to form a coil wire of multiple overlapping segments.

10. The valve of claim 1, wherein the flow restricting portion includes a plurality of spaced apart leaflets extending from the second portion in a direction away from the first portion, the leaflets extending circumferentially around the second portion and foldable inwardly to restrict blood flow, the flow restricting portion further including a membrane joining adjacent leaflets to cooperate with the leaflets to restrict blood flow when the leaflets are in the closed position.

11. The valve of claim 10, wherein the leaflets have a thicker portion at a portion closer to the second portion and the membrane has a thinner portion at a portion further from the second portion.

* * * * *